(12) United States Patent
McFarlane

(10) Patent No.: US 6,478,806 B2
(45) Date of Patent: Nov. 12, 2002

(54) PENETRATING TIP FOR TROCAR ASSEMBLY

(75) Inventor: Richard H. McFarlane, Riviera Bch, FL (US)

(73) Assignee: Taut, Inc., Geneva, IL (US)

( * ) Notice: Subject to any disclaimer, the term of this patent is extended or adjusted under 35 U.S.C. 154(b) by 0 days.

(21) Appl. No.: 09/859,009

(22) Filed: May 16, 2001

(65) Prior Publication Data

US 2002/0013597 A1 Jan. 31, 2002

Related U.S. Application Data

(60) Provisional application No. 60/204,396, filed on May 16, 2000.

(51) Int. Cl.[7] ............................................... A61B 17/32
(52) U.S. Cl. ....................................................... 606/185
(58) Field of Search ........................... 606/1, 184, 185; 604/164.01, 164.04, 264, 272

(56) References Cited

U.S. PATENT DOCUMENTS

| | | | |
|---|---|---|---|
| 3,705,577 A | * 12/1972 | Sierra | |
| 4,561,445 A | 12/1985 | Berke et al. | |
| 4,808,157 A | 2/1989 | Coombs | |
| 5,114,407 A | 5/1992 | Burbank | |
| 5,224,951 A | 7/1993 | Freitas | |
| 5,254,106 A | 10/1993 | Feaster | |
| 5,256,147 A | 10/1993 | Vidal et al. | |
| 5,312,360 A | 5/1994 | Behl | |
| 5,318,580 A | 6/1994 | Gresl, Jr. | |
| 5,352,206 A | 10/1994 | Cushieri et al. | |
| 5,372,588 A | 12/1994 | Farley et al. | |
| 5,390,156 A | * 2/1995 | Hildwein et al. | ............ 606/185 |
| 5,405,328 A | * 4/1995 | Vidal et al. | .................. 604/274 |
| 5,478,328 A | 12/1995 | Silverman et al. | |
| 5,601,559 A | 2/1997 | Melker et al. | |
| 5,624,459 A | 4/1997 | Kortenbach et al. | |
| 5,674,237 A | 10/1997 | Ott | |
| 5,676,681 A | 10/1997 | Yoon | |
| 5,690,663 A | 11/1997 | Stephens | |
| 5,730,754 A | * 3/1998 | Obenchain | ................... 606/185 |
| 5,792,142 A | 8/1998 | Galitzer | |
| 5,807,317 A | 9/1998 | Krech, Jr. | |
| 5,843,039 A | 12/1998 | Klemm | |
| 5,984,919 A | 11/1999 | Hilal et al. | |
| 5,984,941 A | 11/1999 | Wilson et al. | |
| 6,168,607 B1 | * 1/2001 | Wattiez et al. | ............... 606/185 |

* cited by examiner

*Primary Examiner*—Kevin T. Truong
(74) *Attorney, Agent, or Firm*—Malloy & Malloy, P.A.

(57) ABSTRACT

A tissue penetrating instrument of the type used in the medical field and which may or may not be embodied in the form of an obturator associated with a trocar assembly, wherein the instrument includes an elongated shaft having a penetrating tip mounted on one end thereof. The penetrating tip includes a base secured to the one end of the shaft and a distal extremity spaced longitudinally outward from the base and formed into an apex which may be defined by a point or other configuration specifically structured to facilitate penetration or puncturing of bodily tissue. The apex may be substantially aligned with a linear extension of the central longitudinal axis of the shaft or alternatively, may be spaced laterally outward or off-set from the central longitudinal axis of the shaft. The penetrating tip further includes an exterior surface extending continuously between the apex and the base and configured to facilitate puncturing of the tissue and an enlargement of an access opening formed in the tissue, in a manner which facilitates separation of the tissue and minimizes cutting, severing or otherwise damaging the contiguous bodily tissue surrounding the access opening.

24 Claims, 7 Drawing Sheets

PENETRATING TIP FOR TROCAR ASSEMBLY

CLAIM OF PRIORITY

The present application is based on and a claim to priority is made under 35 U.S.C. Section 119(e) to provisional patent application currently pending in the U.S. Patent and Trademark Office having Ser. No. 60/204,396 and a filing date of May 16, 2000.

BACKGROUND OF THE INVENTION

1. Field of the Invention

The present invention is directed towards a medical instrument such as, but not limited to, an obturator of the type associated with a trocar assembly and which includes an elongated shaft having a penetrating tip formed on one end thereof. The penetrating tip includes an exterior surface configuration structured to facilitate the forming of an access opening in bodily tissue in a manner which requires a minimum application of an inwardly directed, linear pushing force on the instrument, but rather relies on a back and forth or "reciprocal" twisting motion. The configuration of the exterior surface of the penetrating tip is at least partially characterized by a perpendicular cross-section, extending along at least a majority of the length of the tip, having a circumferential configuration substantially in the form of an ellipse.

2. Description of the Related Art

In the medical field there are numerous instruments specifically designed to penetrate bodily tissue so as to provide access to internal body cavities or organs. More specifically, an initial and primary activity during the performance of surgery is the creation of an access opening into the body cavity at a predetermined surgical site. In the past, such access openings were formed by the creation of a substantially large incision through the body wall or outer tissue, wherein the size of the incision would depend on the type of surgery, and accordingly, the surgical instruments involved. On completion of the surgical procedure, the large incision would be closed using conventional techniques. However, due to the traumatic nature of such open surgical procedures, the period of time required of the patient to completely heal was significant. In addition, the pain or discomfort during such recuperative period was a serious problem.

Because of the above noted disadvantages, attempts have been made which were specifically directed towards new surgical procedures as well as instruments utilized in the support of such procedures. Currently, a popular alternative to open surgery is known as laparoscopic and/or endoscopic surgery, wherein a number of small openings, utilizing appropriate penetrating instruments, are formed to provide access into an intended body cavities. Unlike the large incision required during open surgery, the much smaller access openings facilitate healing following the surgical and, as expected, result in significantly less discomfort to the patient.

Depending on the type of endoscopic surgery being performed, the instrumentation used to form the one or more small access openings may vary. However, common to such medical penetrating instruments is the provision of a sharpened or otherwise configured penetrating tip. By way of example, instrumentation utilized in the performance of endoscopic surgery are commonly referred to as trocar devices or trocar assemblies. In conventional fashion, a trocar assembly normally includes a trocar tube or cannula and an obturator. Utilizing such instrumentation, access is gained to a body cavity or organ by penetrating the bodily tissue defining the exterior wall of the patient, in order that laparoscopic or arthroscopic surgery may be performed. The obturator, serving as the penetrating instrument, passes along or is positioned within the lumen of the cannula or trocar tube. The aforementioned penetrating tip is formed on the distal end of the obturator. The penetrating tip of the obturator is forced through the skin until entry to the body cavity has been established. The trocar tube, serving as an access cannula is then forced through the perforation, formed by the obturator and the obturator is withdrawn, leaving the trocar tube or cannula as an access or passage way to the intended body cavity or organ.

In related endoscopic surgical techniques, the penetrating instrument may be used with the trocar tube or surgical access cannula or may be used as a "stand alone" device to puncture through the skin and underlying bodily tissue for purposes of forming the small access opening and inserting a separate access cannula, catheter or other surgical instrument into communication with the now accessed body cavity or organ.

The aforementioned substantially conventional medical penetrating instruments normally include a penetrating tip having a sharpened point spaced distally from a base which is connected to one end of the obturator or penetrating instrument. Also the conventional structure of such penetrating tips typically include either a conical or a multi-sided, substantially pyramidal configuration. The design and structuring of penetrating tips for the type of medical instruments described herein is important for the efficient formation of the small access opening, as set forth above. However, such penetrating tips should efficiently and cleanly create the access opening in a manner which serves to at least partially dilate or enlarge the opening, as the shaft of the obturator or other penetrating instrument passes through the bodily tissue. However, it is equally important that a minimal amount of damage, in terms of severing or cutting, be done to the contiguous body tissue surrounding the access opening during the initial penetration, as well as the enlargement of the access opening, as the penetrating instrument is positioned into direct communication with the intended body cavity or organ.

Accordingly, there is a need in the field of medical instrumentation for a penetrating instrument which may be used independently or which may be associated with a trocar device or assembly, along with other associated components such as, but not limited to, a trocar tube or access cannula. Such an improved penetrating instrument should be designed to include an improved penetrating tip which is structured to facilitate a clean formation of a small access opening through the puncturing of the body wall. The penetrating tip should preferably include an exterior surface, as well as a distal extremity or apex, cooperatively or collectively configured to enlarge the access opening and effectively separate or dilate the bodily tissue contiguously disposed to the access opening, as the penetrating instrument is advanced therethrough into communicating relation with a predetermined body cavity or organ. Further, the design and structuring of the penetrating tip should be such as to form the access opening, in the manner set forth above, without causing any unnecessary cutting, severing or damaging of the bodily tissue during the formation of the access opening.

SUMMARY OF THE INVENTION

The present invention is directed towards a penetrating instrument of the type used in the medical field and which may or may not be embodied in a trocar assembly, wherein the penetrating instrument would be specifically referred to as the obturator. Whether or not embodied in a trocar assembly, the penetrating instrument of the present invention comprises a penetrating tip specifically designed and structured to create a small access opening in the body wall or outer tissue of a patient, so as to establish communication with an internal body cavity or organ on which a surgical procedure is to be performed.

Further, the penetrating tip of the present invention is designed and structured to effectively create the small access opening by puncturing the outer body tissue or body wall of a patient in a manner which serves to separate and enlarge the created access opening, as the penetrating instrument passes therethrough into communication with the body cavity. The design and overall structural configuration of the penetrating tip, as will be explained in greater detail hereinafter, is such as to accomplish an effective separation of the bodily tissue being penetrated and at least a minimal dilation of such tissue in a manner which creates a minimal amount of cutting and severing of the body tissue, and thereby, minimizes the damage to the body tissue contiguous to the access opening during its formation or during the passage of an access cannula or other instruments therethrough.

More specifically, the penetrating instrument of the present invention, whether associated with a trocar assembly or used independently thereof, comprises an elongated shaft having a penetrating tip integrally or otherwise secured to an outer end thereof. The penetrating tip includes a base which is integrally or otherwise fixedly secured to the outer end of the shaft. In addition, the penetrating tip includes a distal extremity configured to define an apex. For purposes of clarity, the term "apex" is meant to describe a variety of different configurations, which may vary from a sharpened point to a tapered locale, which may be defined by the converging of the exterior surface of the penetrating tip extending continuously from the base to the distal extremity. In any event, the apex may assume a variety of different configurations, all of which are specifically intended to facilitate the penetration of the body wall or outer tissue in a manner which minimizes any damage being done to the contiguous tissue surrounding a formed access opening created by the penetration or puncturing of the body tissue.

The aforementioned exterior surface of the penetrating tip extends from a convergent locale, defined by the aforementioned apex, continuously to the base of the penetrating tip located at and defining the integral or otherwise fixed junction between the penetrating tip and the outer most end of the shaft of the penetrating instrument. Further, the apex of the penetrating tip, in different embodiments of the present invention, may be disposed coincident to a linear extension of a central longitudinal access of the shaft or, alternatively, may be spaced laterally outward or in an off-set, somewhat eccentric position relative to a linear extension of the central longitudinal access of the shaft of the penetrating instrument.

Common to each of the aforementioned embodiments is a shaping of the exterior surface of the penetrating tip in structural cooperation with the distal extremity or apex thereof, such that a cross-section of the penetrating tip, oriented perpendicular to the central longitudinal access of the shaft and extending along at least a majority of the length of the penetrating tip, is defined by a substantially elliptical circumferential configuration.

It is emphasized that the referred to perpendicular cross-section of each of the penetrating tips of the above referred to alternative embodiments, does not necessarily comprise a circumferential configuration defined by a "true or precise" ellipse. In one or more embodiments of the penetrating tip of the present invention, the exterior surface thereof comprises at least minimally segregated surface segments, somewhat oppositely disposed, and separated by two elongated edges extending from the apex towards the base in a curved configuration. In addition, the opposed edges may be more specifically defined by cutting edges which, along with the distal extremity of the penetrating tip, serve to facilitate the initial puncture of the body wall or bodily tissue, as well as a separation or dilation of the contiguous tissue surrounding the access opening.

Accordingly, the design and structure of the penetrating tip of the present invention, whether or not embodied in a trocar device, includes an exterior surface configuration and a distal extremity shaped to enlarge and/or separate bodily tissue during the insertion of the penetrating instrument into the body wall of the patient. The preferred exterior surface configuration penetrates the designated bodily tissue in a manner which minimizes damage and/or cutting or severing of the tissue during the passage of the penetrating tip, as well as an adjacent portion of the shaft of the penetrating instrument passing through the created access opening.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
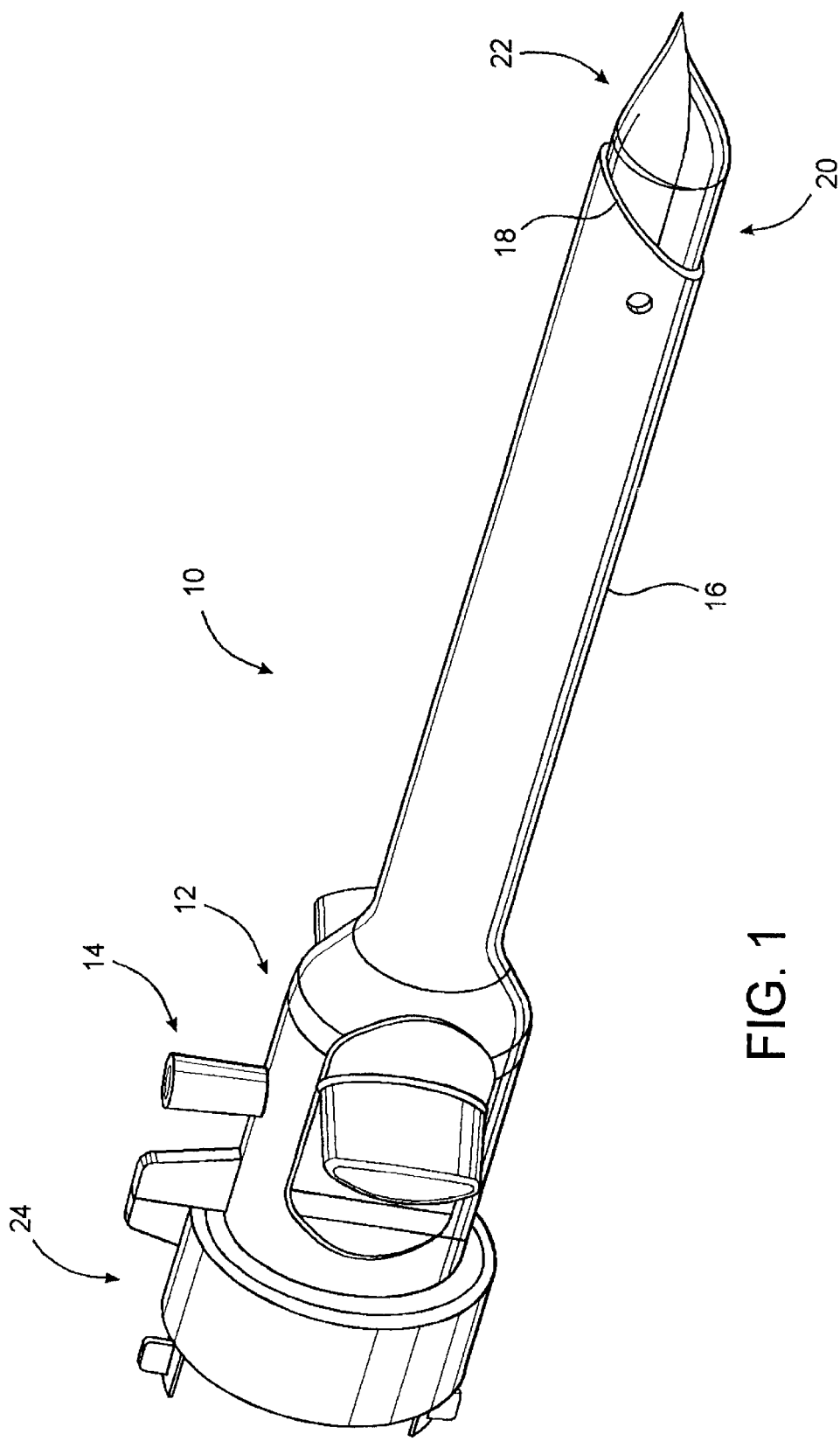
FIG. 1 is a perspective view of the penetrating instrument of the present invention embodied in a trocar assembly.
Figure 2:
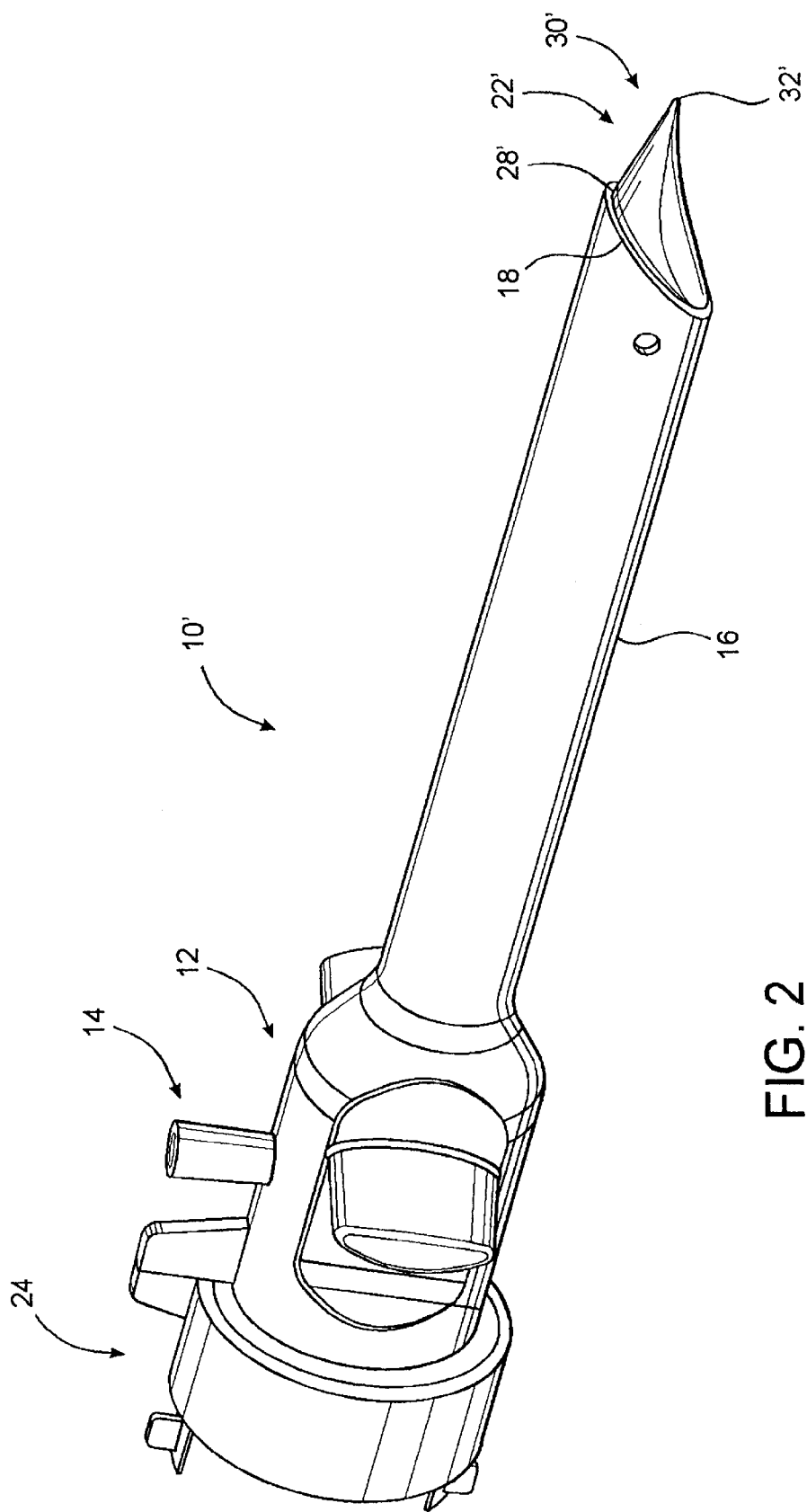
FIG. 2 is another embodiment of the penetrating instrument of the present invention also embodied in a trocar assembly.
Figure 3:
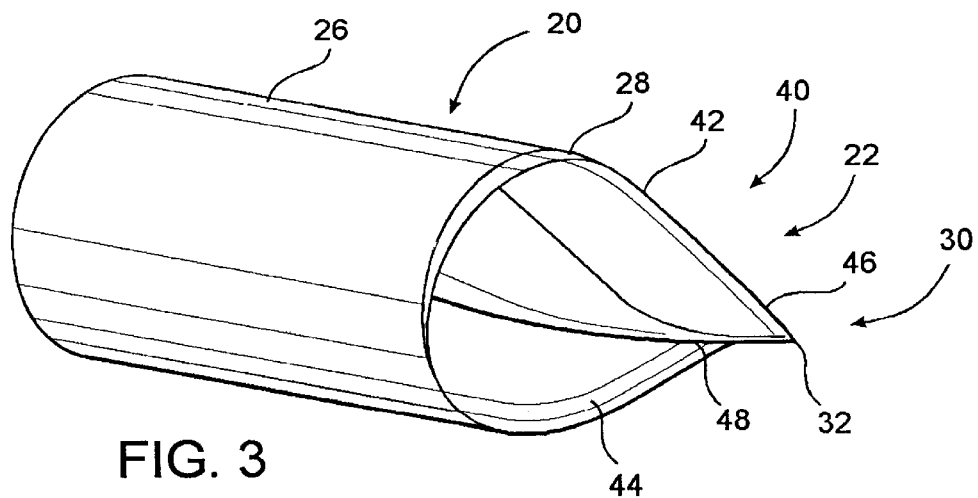
FIG. 3 is a perspective view in partial cutaway of one embodiment of a penetrating tip associated with the present invention.
Figure 4:
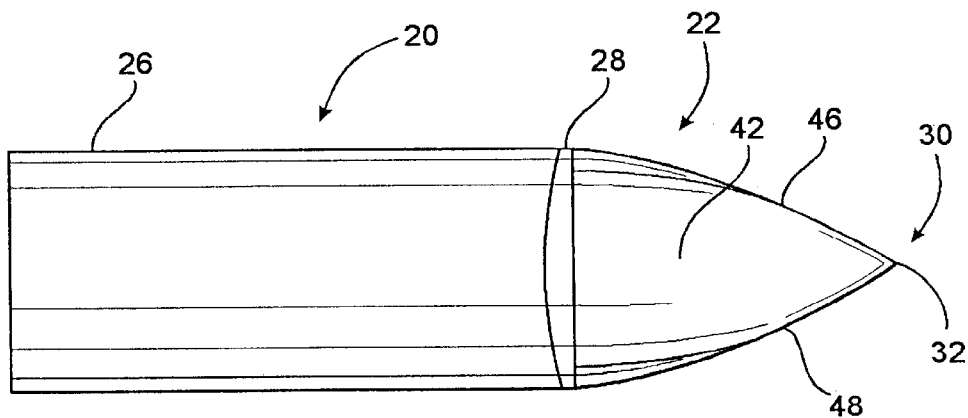
FIG. 4 is a top view of the embodiment of FIG. 3.

As shown in the accompanying Figures, the present invention is directed towards a medical penetrating instrument which may or may not be embodied in a trocar assembly, generally indicated as 10 and 10' respectively, in FIGS. 1 and 2. However, when so embodied, the trocar assembly 10 and 10' typically includes a trocar housing 12, which may include a connector structure 14 communicating with the interior of the housing 12 and structured to establish fluid communication and/or interconnection with a supply of fluid, such as carbon dioxide gas, used to inflate a body cavity as typically performed during endoscopic surgery. Trocar assembly 10 also includes an elongated trocar tube or cannula 16 designed to removably receive the penetrating instrument, generally indicated as 20, along the centrally disposed lumen associated with the tube or cannula 16. The obturator or penetrating instrument 20 has a penetrating tip generally indicated as 22 extending outwardly from the open end 18 of the cannula 16. The trocar assemblies 10 and 10' may have substantially equivalent structures and differ from one another primarily in the structural configuration of the obturator or penetrating instruments 20 and 20' and specifically the structure of the respective penetrating tips 22 and 22'. Further, in each of the embodiments of FIGS. 1 and 2 a mounting hub as at 24 is secured to one end of the penetrating instrument 20 and 20' opposite to the penetrating tip 22 and 22', wherein the hub 24 is associated for interconnection with the housing 12.

Further structural components common to both the embodiments of FIGS. 1 and 2 is the provision of an elongated shaft 26, having one distal end integrally or otherwise fixedly secured to the corresponding tip 22 or 22' and the other end secured to the hub 24, as set forth above. While the elongated shaft 26 and 26' of each of the penetrating instruments 20 and 20' are primarily described as including a solid material construction, it is emphasized herein that the elongated shaft 26 and 26', whether associated with the respective trocar assemblies 101 and 10' or used independently thereof, may also include a substantially hollow, elongated configuration terminating in the respective penetrating tips 22 and 22', which also may be hollow or at least partially hollow. When so structured, the interior of the elongated shaft 26 and 26', as well as the corresponding penetrating tip 22 and 22', are dimensioned and configured to receive conventional or customized instrumentation such as, but not limited to, an endoscope or other illuminating and/or imaging instrumentation designed to facilitate the visual observation of the body cavity, accessed by the penetrating instrument 20 and 20' and/or an access cannula 16, which may or may be associated with the trocar assembly 10 and 10'.

With primary reference to the embodiment of FIGS. 1 and 3 through 5, the penetrating instrument 20 of the present invention comprises the penetrating tip 22 having a base 28 integrally or otherwise fixedly secured to the outermost or distal end of the elongated shaft 26. The opposite end of the penetrating tip 22 terminates in a distal extremity generally indicated as 30. Further, the penetrating tip 22 has an exterior surface extending continuously between the base 28 and the distal extremity 30. The distal extremity 30 may be more specifically defined as an apex 32 which is generally configured to assume a blunt point configuration. However, the apex may also assume a variety of other configurations such as that shown in the embodiment of FIG. 2 and indicated as 32'. It is emphasized that the term "point" is not meant to define a true sharpened point structure. To the contrary, apex 32 and/or 32' should be sufficiently blunt to eliminate or significantly reduce the danger of inadvertent penetration or puncturing of any body organ once the penetrating tip passes through exterior bodily tissue and enters an interior cavity of the body. In that the apex 32 and 32' may assume a variety of structural configurations, all of which are intended to facilitate the clean efficient passage of the tips 22 and 22' through the outer body wall or bodily tissue of a patient, the term apex, rather than point, is used to generically and more accurately describe each of the plurality of configurations. Further the apex 32 and 32', regardless of its specific shape, may be defined as a convergent locale of the exterior surface of each of the penetrating tips 22 and 22' as the exterior surface extends from the respective bases 28 and 28' to and including the distal extremity 30 and 30'. The embodiment of FIGS. 1 and 3 through 5 is further defined by the distal extremity 30, and more specifically, the apex 32 being disposed coincident with the central, longitudinal axis of the shaft 26, or more precisely a linear extension of this central longitudinal axis. Further, this embodiment comprises the exterior surface 40 preferably defined by two surface segments 42 and 44. As shown, each of the surface segments 42 and 44 have a somewhat symmetrical configuration and are at least minimally segregated by two at least partially, oppositely disposed and curved edges 46 and 48. In yet another embodiment of the present invention the edges 46 and 48 are specifically shaped or configured to define cutting edges and extend from the apex 32 back towards the base 28 along at least a major length of the penetrating tip 22 between the apex 32 and the base 28.

Another structural feature of the penetrating tip 22 is the longitudinal configuration of each of the surface segments 42 and 44 to have a curvilinear configuration at least partially defined by a complex curve. In turn, the complex curvilinear configuration of each of the surface segments 42 and 44, as viewed longitudinally from the apex 32 to the base 28, comprises at least one substantially concave segment 49 and either a linear or minimally convex curve portion or section 49'. As a result, the overall configuration of the exterior surface of the penetrating tip 22 and its cooperative structuring with the apex 32 facilitates the forming and subsequent enlargement of an access opening in the body wall of a patient in a manner which minimizes cutting, severing or otherwise damaging the contiguous bodily tissue surrounding and/or associated with the formed access opening as the penetrating tip ,22 as well as a portion of the shaft 26 passes through the access opening into communication with an intended body cavity.

Figure 5:
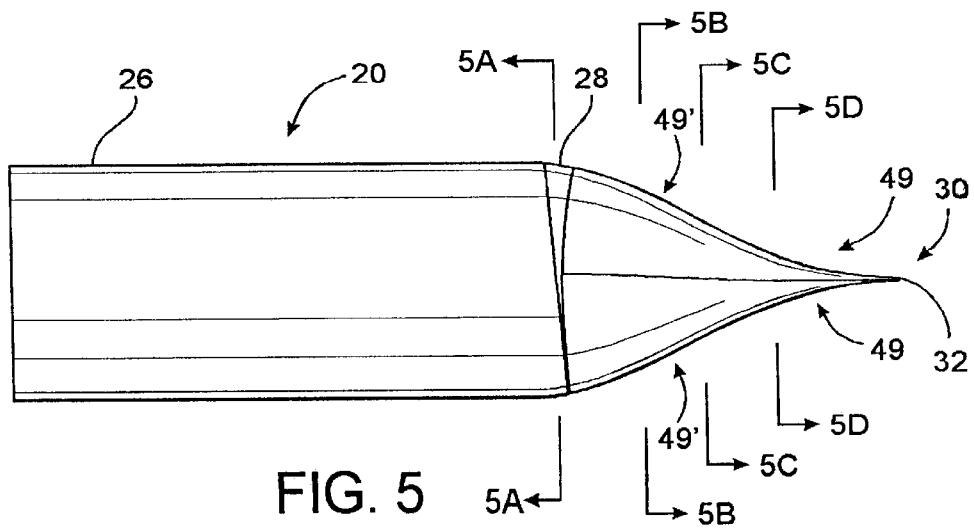
FIG. 5 is a side view of the embodiment of FIGS. 3 and 4.
Figure 5A:
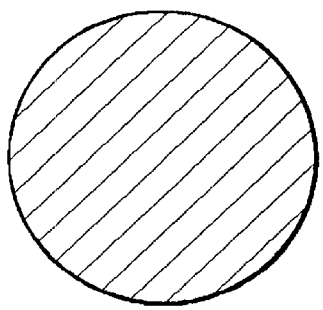
FIGS. 5A, 5B, 5C and 5D are sectional views taken along lines 5A—5A, 5B—5B, 5C—5C, and 5D—5D, respectively.
Figure 5B:
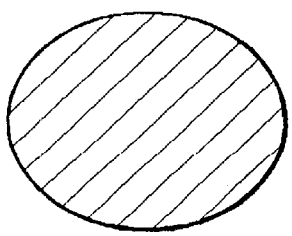
Figure 5C:
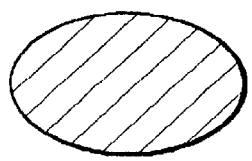
Figure 5D:

The penetrating tip therefore may be further characterized by having a cross-section, which is oriented perpendicular to the central longitudinal axis of the shaft 26 and extends along at least a majority of the length of the penetrating tip 22, defined by a substantially elliptical configuration as evidenced by the representative cross-sectional configurations in FIGS. 5B, 5C and 5D. By way of reference, the perpendicular cross-sectional configuration of the base 28, taken along the imaginary line 5A—5A, is defined by a circumferential configuration in the form of a circle. As set forth above, the circumferential configuration of anyone of an infinite number of perpendicular cross-sections, extending along the majority of the length of the penetrating tip 22 between the apex 32 and the base 28, are defined by a substantially elliptical configuration, as schematically represented in FIGS. 5B, 5C, and 5D.

It is emphasized that the circumferential configurations shown in FIGS. 5B through 5D are generally representative only. It is acknowledged that the true circumferential configuration of the various perpendicular sections oriented along the majority of the length of the penetrating tip 22, are not necessarily true or precise ellipses. This is due to the existence of the aforementioned segregating edges 46 and 48, which may or may not be structured to serve as cutting edges and which at least minimally segregate the surface segments 42 and 44 from one another. Accordingly, the opposite ends of each of the representative elliptical configurations shown in FIGS. 5B, 5C, and 5D may be slightly varied to more accurately represent the inclusion of the edges 46 and 48. It is further emphasized that these edges may themselves vary in cross-sectional configuration from a true cutting edge, as best demonstrated in FIG. 3, to a more rounded configuration, as indicated by the representative elliptical shapes of FIGS. 5B, 5C and 5D.

It is emphasized that the structural features of each embodiment of the present invention provide for an efficient penetration of the outer bodily tissue and the passage of the penetrating tip and associated shaft there through in a manner which minimizes the danger of inadvertent puncturing of internal organs. More specifically, such initial penetration and passage of the either of the tips 22 and 22' as well as the respective shafts 26 and 26' is accomplished by the exertion of only a minimal amount of linearly directed "pushing" force on the instrument. Instead, penetration is accomplished by applying a twisting motion and preferably a back and forth or "reciprocal twisting" motion to the device Therefore, utilization of each of the embodiments in this manner, plus the provision of a blunted apex 32 or 32', minimizes the chance of inadvertently puncturing and thereby damaging an internal organ subsequent to the penetrating tip 22 or 22' passing through the exterior bodily tissue and into the cavity in which such an organ may be located.

With primary reference to the embodiment of FIGS. 2 and 6 through 8, it is clearly shown that at least one distinguishing structural feature of this embodiment, is the location of the apex 32' in an eccentric or laterally spaced, off-set relation to an imaginary co-linear extension of the central longitudinal axis of the shaft 26'. Accordingly, the exterior surface 40' comprises the two surface segments 42' and 44' which are non-symmetrical, in that surface segment 42' has a significantly smaller overall dimension than that of the surface segment 44'. As a result, the base 28' has a circumferential configuration preferably defined by an elongated ellipse, depicted in FIG. 8A and taken along lines 8A—8A of FIG. 8. Similar to the embodiment of FIGS. 1 and 3 through 5, both of the exterior surface segments 42' and 44' have a longitudinal curvilinear configuration defined by a longitudinally oriented complex curve including at least a minimally concave portion 49'' and a linear portion 49'''. Similarly, the surface segments 42' and 44' are at least minimally segregated from one another through the provision of the elongated curved edges 46' and 48', extending from the apex 32' towards the base 28' and at least along a majority of the length of the penetrating tip 22'. The edges 46' and 48' may have a more rounded or transversely curved configuration than that of the embodiment of FIG. 3, thereby providing a somewhat "blunted" edge configuration 46' and 48' which, differs from the cutting edges 46 and 48 of the embodiment of FIG. 3. However, the exterior surface 40' of the embodiment of FIGS. 2 and 6 through 8 is structured to define an overall exterior surface configuration shaped to enlarge or at least partially dilate an access opening formed in the outer body wall by the penetrating tip 22', while minimizing any cutting, severing or damaging of the contiguous bodily tissue surrounding the formed access opening. Such a preferred structural configuration is further demonstrated in FIGS. 8B, 8C and 8D which represent a transverse circumferential configuration of the exterior surface 40' as being substantially elliptical. As with the embodiment of FIGS. 1 and 3 through 5, the opposite ends of the representative elliptical configurations of the perpendicular cross-sections of the penetrating tip 22' shown in FIGS. 8B, 8C, and 8D, may be more precisely represented by narrowing the opposite ends to more accurately represent the edges 46' and 48'. Also, since the apex 32' is laterally off-set from the central longitudinal axis of the shaft 26', the apex 32' is not centered or centrally coincident with any of the elliptically configured cross-sections represented in FIGS. 8A through 8D. To the contrary, in the embodiment of FIG. 5, the apex 32 is coincident to the central longitudinal axis of the shaft 26 and would therefore be substantially centered relative to the circular cross-section of the base 28, as shown in FIG. 5A, as well as the elliptically configured cross-sections of FIGS. 5B through 5D.

Another preferred embodiment of the penetrating instrument of the present invention is shown in FIGS. 9 through 12 and comprises the penetrating instrument 60 including an elongated shaft 62 having a penetrating tip 64 secured to and defining the distal end of shaft 62. Penetrating tip 64 includes a base 66, which in the preferred embodiments of FIGS. 9 through 12, is extended along a predetermined angular orientation of preferably 45 degrees relative to a central longitudinal axis of the shaft 62, schematically indicated as 68. The base 66 is integrally or otherwise fixedly secured to the outer most distal end of the elongated shaft 62 as shown. The opposite end of the penetrating tip 64 terminates in a distal extremity generally indicated as 70 and more specifically defined by an apex 72. Further one feature of this embodiment of the present invention is the disposition of the apex 72 coincident with the central longitudinal axis 68 of the shaft 62, or more precisely, a linear extension 68' of the central longitudinal axis 68.

Additional structural features of this preferred embodiment include the exterior surface 74 including longitudinal extending, curved exterior surface segments 76 and 78. Due at least in part to the angular orientation of the base 66, the exterior surface segments 76 and 78 are of different dimensions, as best shown in FIG. 10, and are non-symmetrical eventhough the apex 72 is disposed coincident with the central longitudinal axis 68 or the linear extension thereof 68'.

Figure 10:
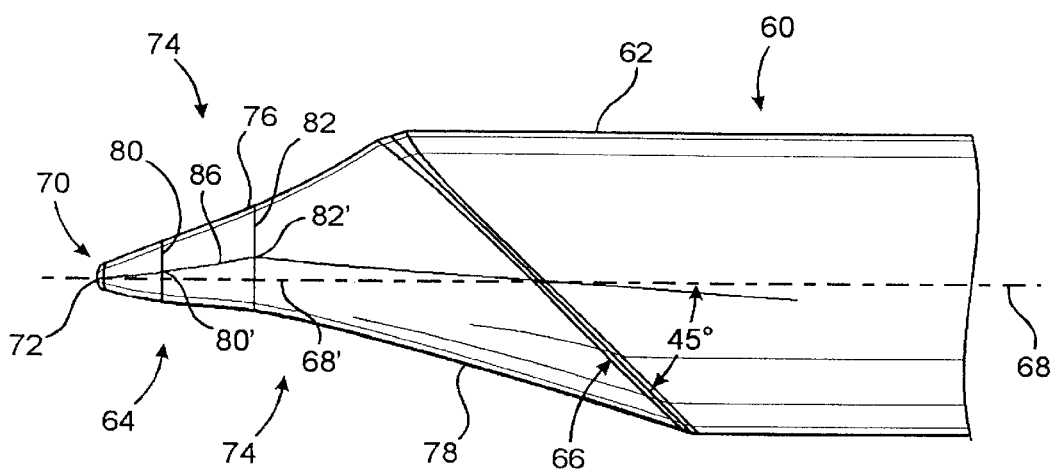
FIG. 10 is a side view of the embodiment of FIG. 9.
Figure 11:
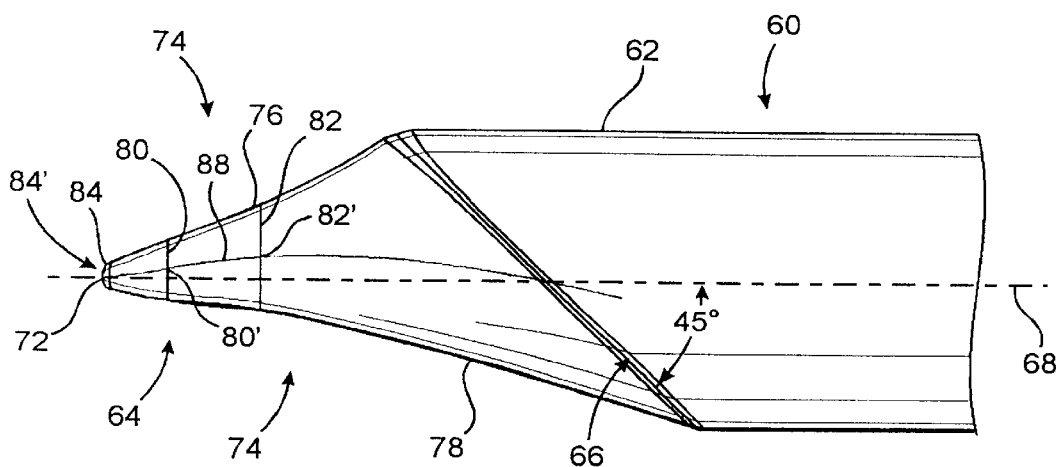
FIG. 11 is a side view of structural variation of the embodiment of FIG. 10.

With primary reference to both FIGS. 10 and 11, the exterior surface 74 of the penetrating tip 64, particularly including the exterior surface segments 76 and 78, can define an at least partially concave, convex and/or complex, longitudinal extending curve. As a result, the perpendicular cross-sectional configuration of the penetrating tip 64, such as along schematic cross-section lines 80 and 82, comprises a substantially elliptical configuration. These elliptical configurations of sections 80 and 82 may be similar to the elliptical cross-sectional configurations as generally disclosed in FIGS. 5B through 5D and/or 8B through 8D of the corresponding embodiments. The structural difference of the embodiment of FIGS. 9 through 12 being that the apex 72 is coincident with the longitudinal axis 68, 68' of the shaft 62 rather than being off-set therefrom. In addition the complex curve of at least one of the exterior surface segments 76 or 78 may best include an elongated concave configuration extending from the apex 70 to towards the base 66 in order to facilitate the penetrating capabilities of the penetrating tip 64. Such a concave configuration of one or both of the exterior surface segments 74 and 76 may be important especially when the apex 72 assumes a more blunted shape which is clearly distinguishable from a sharpened point.

It is further emphasized that the exterior surface 74, including the exterior surface segments 76 and 78 may vary greatly from that shown in FIGS. 10 and 11. Accordingly, dependent upon the configurations of the exterior surface 74, any of an infinite number of perpendicular sections such as those taken along schematic lines 80 and 82 will have the aforementioned elliptical configuration. Also the centers as at 80' and 82' of the respective elliptical configurations as shown in FIGS. 10 and 11 may be disposed along an imaginary straight line as at 86 and/or along an imaginary curved line as at 88.

As set forth above, the apex 72 may be somewhat blunted rather than a true sharpened point and thereby be at least partially defined by an end ellipse 84. Again, the location of the centers 80' and 82' as well as the center 84' of the end ellipse 84 may be disposed along a straight line 86 or a curved line 88 depending, at least in part, on the overall exterior surface configuration 74 while the apex and/or the center point 84' of the end ellipse 84 remains coincident with the longitudinal axis 68, 68'.

Figure 12:
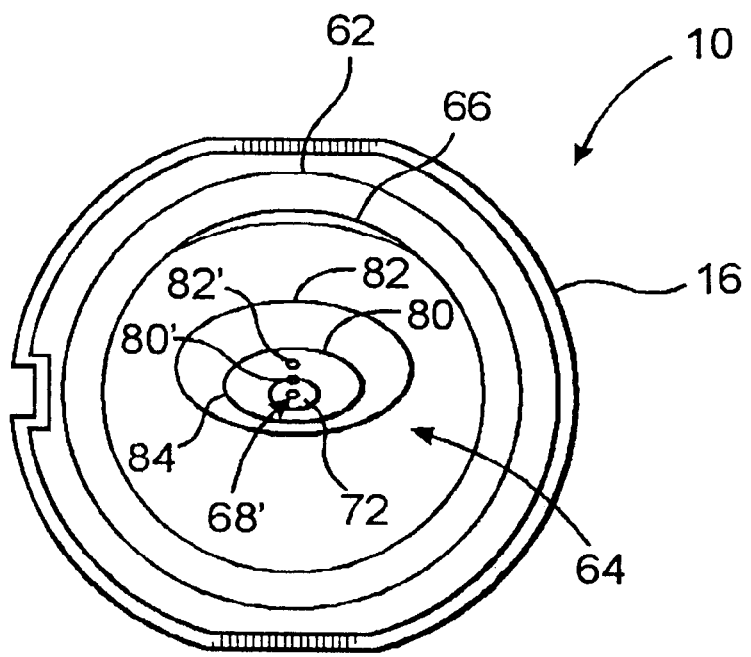
FIG. 12 is a front end view of the embodiment of FIGS. 9 through 11.

Naturally, as with the embodiments of FIGS. 1 through 8, the penetrating instrument 60 may be of the type to be used in combination with a trocar assembly generally indicated as 10 including the elongated trocar tube as shown in both FIGS. 1 and 12. However, the penetrating instrument may be adaptable for use in other medical procedures.

Figure 8A:
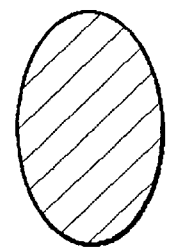
FIGS. 8A, 8B, 8C, and 8D are sectional views taken along lines 8A—8A, 8B—8B, 8C—8C, and 8D—8D, respectively.
Figure 8B:
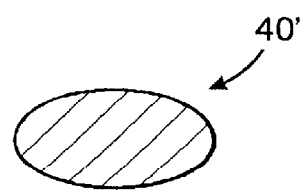
Figure 8C:
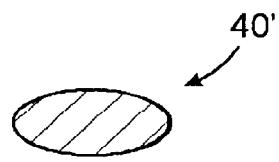
Figure 8D:
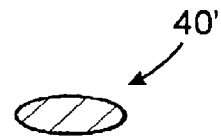
Figure 6:
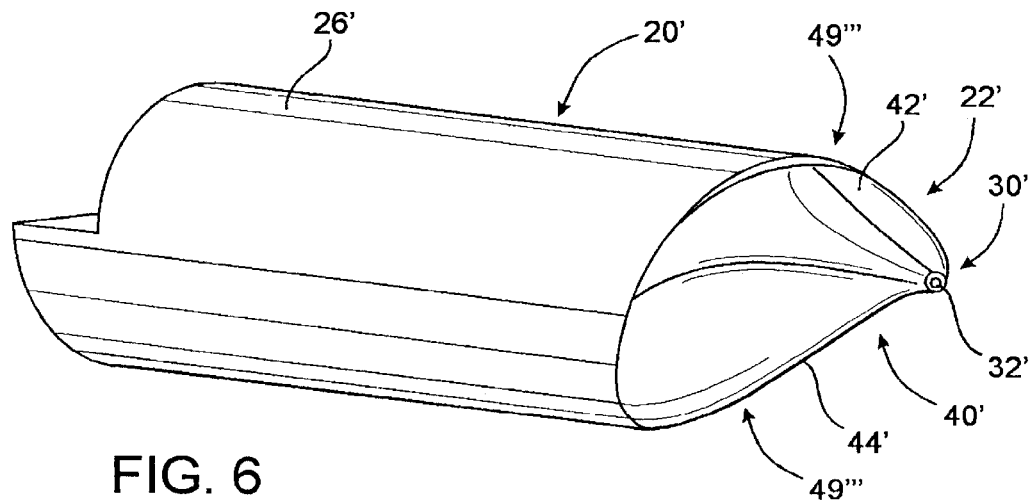
FIG. 6 is a perspective view in partial cutaway of another embodiment of a penetrating tip associated with the present invention.
Figure 7:
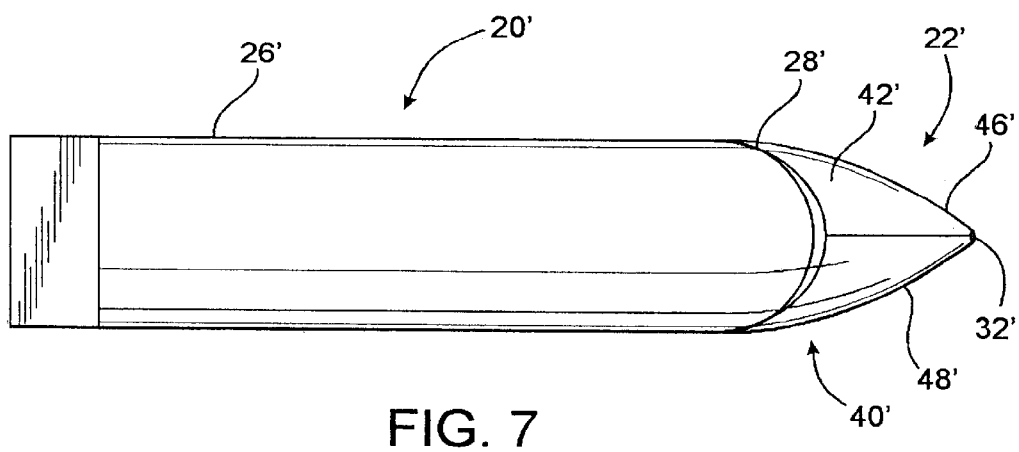
FIG. 7 is a top view in partial cutaway of the embodiment of FIG. 6.
Figure 8:
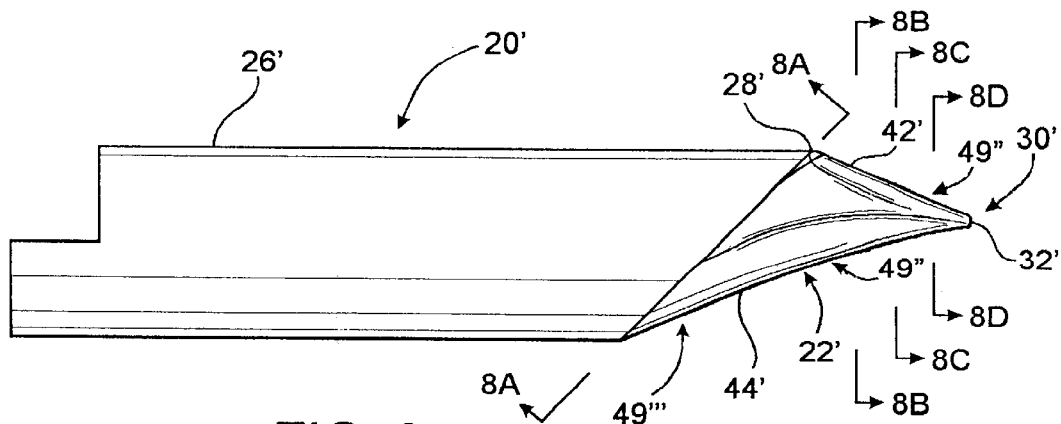
FIG. 8 is a side view in partial cutaway of the embodiment of FIGS. 6 and 7.
Figure 9:
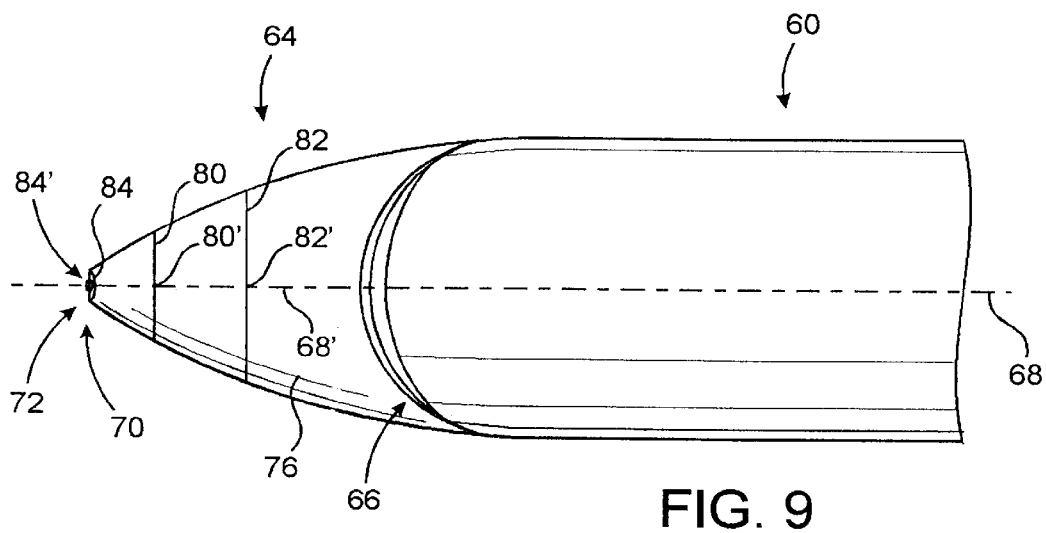
FIG. 9 is a top view of another preferred embodiment of a penetrating instrument of the present invention including a penetrating tip and associated shaft, in partial cutaway.

It is also noted that the base 66 being angularly oriented at a preferred angle of 45 degrees relative to the longitudinal axis 68 and 68' defines an elliptical configuration somewhat similar to that shown in the embodiment of FIG. 8A. The precise shape of the preferred elliptical configuration will of course vary, dependent on the angular orientation of the base 66 relative to the longitudinal axis 68 being greater or less than the preferred 45 degree angle of incline, as indicated.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A tissue penetrating medical instrument structured to be used with a trocar tube, said instrument comprising:
   a) an obturator comprising an elongated shaft and including a penetrating tip disposed at one end of said shaft,
   b) said penetrating tip including a base disposed at said one end and an apex extending outwardly in spaced relation to said base,
   c) said penetrating tip further including an exterior surface extending between said base and said apex,
   d) said exterior surface having a cross-section oriented perpendicular to a central longitudinal axis of said shaft and extending along at least a majority of a length of said penetrating tip and being defined by a substantially elliptical circumferential configuration,
   e) said exterior surface comprising a curvilinear configuration extending longitudinally between said apex and said base and being at least partially defined by a complex curve extending along at least a majority of a length thereof, and
   f) said complex curve comprising a substantially concave curve segment extending outwardly from said apex towards said base.

2. An instrument as recited in claim 1 wherein said exterior surface comprises two surface segments each extending longitudinally between said apex and said base, said two surface segments being at least minimally segregated from one another.

3. An instrument as recited in claim 2 further comprising a segregating junction disposed between said two surface segments.

4. An instrument as recited in claim 3 wherein said segregating junction comprises two elongated edges having a curved configuration and extending from said apex towards said base.

5. An instrument as recited in claim 4 wherein each of said edges comprises a substantially convex configuration shaped into a cutting edge.

6. An instrument as recited in claim 5 wherein each of said two surface segments comprises a substantially concave configuration extending along at least a majority of its length.

7. An instrument as recited in claim 6 wherein said apex is linearly coincident with said central longitudinal axis of said shaft.

8. An instrument as recited in claim 7 wherein said two surface segments are substantially symmetrical.

9. An instrument as recited in claim 8 wherein said base comprises a substantially circular circumferential configuration.

10. A tissue penetrating medical instrument comprising:
    a) an elongated shaft having a penetrating tip disposed at one end thereof,
    b) said penetrating tip including a base disposed at said one end of said shaft and an apex extending outwardly in spaced relation from said base,
    c) said penetrating tip further including an exterior surface extending between said base and said apex,
    d) said apex disposed coincident to a linear extension of a central longitudinal axis of said shaft,
    e) said exterior surface having a cross-section oriented perpendicular to a central longitudinal axis of said shaft and extending along at least a majority of said penetrating tip and being defined by a substantially elliptical circumferential configuration, and
    f) said exterior surface comprising at least two surface segments each extending longitudinally between said apex and said base, each surface segment comprising a substantially concave configuration extending along at least a portion of a length thereof.

11. An instrument as recited in claim 10 wherein said base comprises a substantially circular circumferential configuration.

12. An instrument as recited in claim 10 wherein said exterior surface comprises a curvilinear configuration extending longitudinal along a majority of the length between said base and said apex and comprising a complex curve extending along a majority of the length thereof.

13. An instrument as recited in claim 12 wherein said complex curve is at least partially defined by said concave configuration of at least one of said curve segments extending outwardly from said apex towards said base.

14. A tissue penetrating medical instrument comprising:
   a) an elongated shaft having a penetrating tip disposed on one end thereof,
   b) said penetrating tip including a base formed on said one end and an apex extending outwardly in spaced relation to said base,
   c) said penetrating tip further including an exterior surface extending between said base and said apex,
   d) said apex disposed coincident to a linear extension of a central longitudinal axis of said shaft and said base being disposed at a predetermined angular orientation of substantially 45 degrees relative to said central longitudinal access of said shaft, and
   e) said penetrating tip comprising a substantially continuously elliptical cross-sectional configuration oriented perpendicular to a central longitudinal axis of said shaft and extending along at least the majority of its length.

15. An instrument as recited in claim 14 wherein said exterior surface comprises a curvilinear configuration extending along a majority of its length between said base and said apex; said curvilinear configuration extending longitudinally between said apex and said base and comprising a complex curve extending along a majority of the length thereof.

16. An instrument as recited in claim 15 wherein said complex curve comprises a substantially concave curve segment extending along at least a portion of the length thereof and outwardly from said apex towards said base.

17. An instrument as recited in claim 16 wherein said exterior surface comprises two surface segments each extending longitudinally between said apex and said base, said two surface segments being at least minimally segregated from one another.

18. An instrument as recited in claim 17 wherein each of said two surface segments comprises a substantially concave configuration extending from said distal extremity towards said base and along at least a majority of their respective lengths.

19. A tissue penetrating medical instrument structured to be used with a trocar tube, said instrument comprising:
   a) an obturator comprising an elongated shaft and including a penetrating tip disposed at one end of said shaft,
   b) said penetrating tip including a base being disposed at said one end of said shaft and an apex being linearly coincident with a central longitudinal axis of said shaft and extending outwardly in spaced relation to said base,
   c) said penetrating tip further including an exterior surface extending between said base and said apex,
   d) said exterior surface having a cross-section oriented perpendicular to said central longitudinal axis of said shaft and extending along at least a majority of a length of said penetrating tip and being defined by a substantially elliptical circumferential configuration, and
   e) said base being disposed at a predetermined angular orientation relative to said central longitudinal axis of said shaft.

20. An instrument as recited in claim 19 wherein said predetermined angular orientation is substantially 45 degrees.

21. A tissue penetrating medical instrument structured to be used with a trocar tube, said instrument comprising:
   a) an obturator comprising an elongated shaft and including a penetrating tip disposed at one end of said shaft,
   b) said penetrating tip including a base being disposed at said one end of said shaft and an apex being linearly coincident with a central longitudinal axis of said shaft and extending outwardly in spaced relation to said base,
   c) said penetrating tip further including an exterior surface comprising two surface segments extending between said base and said apex, said two surface segments having different lengths, and
   d) said exterior surface having a cross-section oriented perpendicular to said central longitudinal axis of said shaft and extending along at least a majority of a length of said penetrating tip and being defined by a substantially elliptical circumferential configuration.

22. A tissue penetrating medical instrument structured to be used with a trocar tube, said instrument comprising:
   a) an obturator comprising an elongated shaft and including a penetrating tip disposed at one end of said shaft,
   b) said penetrating tip including a base disposed at said one end and an apex extending outwardly in spaced relation to said base,
   c) said penetrating tip further including an exterior surface extending between said base and said apex, said exterior surface comprising two surface segments each extending longitudinally between said apex and said base, each of said two surface segments comprising a substantially concave configuration extending along at least a portion of its length, and
   d) said exterior surface having a cross-section oriented perpendicular to a central longitudinal axis of said shaft and extending along at least a majority of a length of said penetrating tip and being defined by a substantially elliptical circumferential configuration.

23. An instrument as recited in claim 22 wherein said apex is disposed at a converging locale of said exterior surface; said apex being disposed in a linearly coincident relation to said central longitudinal axis of said shaft.

24. An instrument as recited in claim 23 wherein said base comprises a substantially elliptical circumferential configuration.

* * * * *